United States Patent [19]

Kraff

[11] Patent Number: 4,799,483
[45] Date of Patent: Jan. 24, 1989

[54] SUTURING NEEDLE WITH TAIL MOUNTED CUTTING BLADE AND METHOD FOR USING SAME

[76] Inventor: Manus C. Kraff, 5600 W. Addison, Chicago, Ill. 60634

[21] Appl. No.: 154,985

[22] Filed: Feb. 11, 1988

[51] Int. Cl.⁴ .............................................. A61B 17/06
[52] U.S. Cl. .................... 128/339; 128/335.5
[58] Field of Search .................. 128/339, 335.5, 335

[56] References Cited

U.S. PATENT DOCUMENTS

| | | |
|---|---|---|
| 527,263 | 10/1894 | Blanchard . |
| 856,686 | 6/1907 | Edwards . |
| 1,377,359 | 5/1921 | Littlejohn . |
| 1,592,897 | 7/1926 | Morton . |
| 2,240,330 | 4/1941 | Flagg et al. ............... 128/339 |
| 2,591,063 | 4/1952 | Goldberg ................... 128/334 |
| 2,811,157 | 10/1957 | Kurtz et al. ............... 128/339 |
| 2,841,150 | 7/1958 | Riall .......................... 128/339 |
| 2,869,550 | 1/1959 | Kurtz .......................... 128/339 |
| 3,038,475 | 6/1962 | Orcutt ........................ 128/339 |
| 3,094,123 | 6/1963 | Kurtz .......................... 128/339 |
| 3,160,157 | 12/1964 | Chisman ..................... 128/339 |
| 3,238,942 | 3/1966 | Lincoff ........................ 128/339 |
| 3,556,953 | 1/1971 | Schultz ....................... 204/20 |
| 3,636,955 | 1/1972 | Kurtz .......................... 128/305 |
| 3,799,169 | 3/1974 | Beroff et al. ............... 128/339 |
| 3,892,240 | 7/1975 | Park ............................ 128/339 |
| 3,924,630 | 12/1975 | Walldorf .................... 128/339 |
| 4,237,892 | 12/1980 | Ritter et al. ................ 128/339 |
| 4,345,601 | 8/1982 | Fukuda ....................... 128/339 |
| 4,524,771 | 6/1985 | McGregor et al. ......... 128/339 |
| 4,527,564 | 7/1985 | Eguchi et al. .............. 128/339 |

Primary Examiner—Richard C. Pinkham
Assistant Examiner—Gary Jackson
Attorney, Agent, or Firm—Dick and Harris

[57] ABSTRACT

A curved surgical needle for tissue wound closure and in particular, suturing together both sides of an incision made in human or animal tissue comprising a substantially curved body portion, a point located at a first end, suturing material attached at an opposite tail end, and at least one cutting blade projecting radially outwardly from the tail end so as to make a radial cut in the tissue to facilitate the entry and passage of the suturing material through the tissue, as well as to facilitate rotation of the knotted suture for purposes of burying the knot below the surface of the tissue.

13 Claims, 1 Drawing Sheet

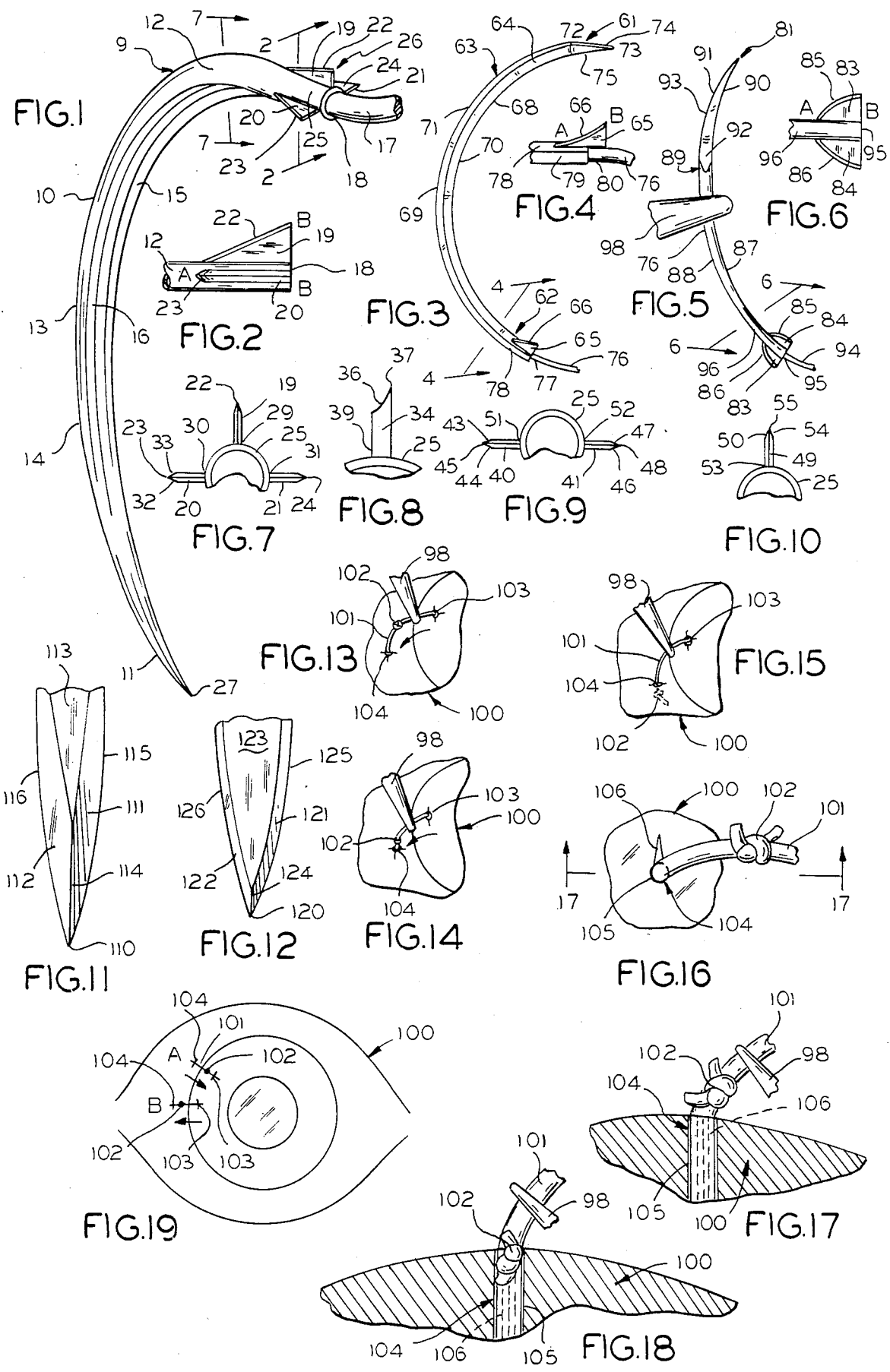

SUTURING NEEDLE WITH TAIL MOUNTED CUTTING BLADE AND METHOD FOR USING SAME

BACKGROUND OF THE INVENTION

The present invention relates in general to surgical instruments, and in particular, to a curved surgical needle used for tissue wound closure and in particular, suturing together an incision made in human or animal tissue during ophthalmic or other types of microsurgery.

For decades, various types and configurations of surgical needles having suture material attached thereto in a variety of ways, have been used for purposes of closing incisions made during various types of surgery. Among such prior art surgical needles are U.S. Pat. Nos.: 856,686; 1,592,897; 2,591,063; 2,811,157; 2,869,550; 3,094,123; 3,160,157; 3,238,942; 3,556,953; and 3,799,769.

Few, if any, such conventional suturing needles have attempted to address the problem of facilitating the passage of the tail portion of such a needle through the tissue being sutured. Moreover, such prior art surgical needles have not successfully addressed the problem of facilitating rotation of a knotted suture so as to "bury" the knot below the surface of the tissue, thereby reducing anticipated, perceived and actual irritation of surrounding tissue.

It is such an object of the present invention to provide a surgical suturing needle having a construction which facilitates passage of the needle, and in particular, the tail portion thereof having the suturing material emanating therefrom which is normally the area encountering the most resistance, through the tissue being sutured.

It is further an object of the present invention to provide a surgical suturing needle having a construction serving to provide a track through the tissue being sutured which facilitates passage of the suturing material therethrough, while minimizing the trauma caused to the surrounding tissue.

It is also an object of the present invention to provide a surgical suturing needle having a construction which facilitates rotation of a knotted suture so as to "bury" the knot below the surface of the tissue, to thereby overcome the reluctance or inability of many surgeons to perform such a desired surgical technique which reduces the risk of rupturing the surrounding tissue or tearing the suture.

It is yet another object of the present invention to provide a surgical suturing needle having a construction wherein the body portion of the needle between the point and the tail is devoid of cutting surfaces so as to enable the tissue being sutured to momentarily recover after the shock of being pierced by the tip of the needle before radial incisions are made by blades mounted proximate the tail of the suturing needle.

It is also an object of the present invention to provide a surgical suturing needle construction which is relatively inexpensive and easy to manufacture.

These and other objects of the present invention will become apparent in light of the present specification and drawings.

SUMMARY OF THE INVENTION

The present invention comprises a curved surgical needle for tissue wound closure, and in particular, suturing together both sides of an incision made in human or animal tissue. The surgical needle has an inner concave surface and an outer convex surface and has suturing material securely attachable thereto. The aforementioned needle comprises a substantially curved body portion having first and second ends. A point is located at the first end of the body portion for piercing the tissue on opposite sides of the incision, and forming an axial passage or bore in the tissue for the suturing material to pass through and thereby draw both sides of the incision together, when the ends of the suture material are tied or otherwise drawn together. Suture attachment means are positioned at the second end of the body portion and are adapted for receiving, securing and maintaining the suturing material upon the needle. The needle further has a tail portion proximate the body portion second end. Also, the needle has an intermediate portion between the point and the tail portion which is devoid of cutting surfaces. In addition, the tail portion has cutting edge means projecting radially outwardly from it for making at least one radial cut in the tissue extending from the axial passageway so as to facilitate the entry and passage of the suturing material through the tissue.

The present invention can also include at least one cutting edge proximate the first end of the body portion. Moreover, in a first preferred embodiment, the intermediate portion of the body portion can be substantially circular in cross-section. In addition, the cross-sectional area of the body portion of the present invention can increase as one moves from the first end and through the intermediate portion. Moreover, the present invention can also include a substantially flattened area on the concave surface thereof between the first end and the second end of the body portion. Similarly, the cutting edge means provided on the tail portion of the present invention can include at least one blade operably attached to the tail portion.

In a first preferred embodiment, the tail portion cutting edge means can comprise a single blade projecting outwardly in a radial direction from the outer periphery of the tail portion. Furthermore, in another embodiment, the tail portion cutting edge means can comprise two or more blades projecting outwardly from opposite sides of the outer periphery of the tail portion. In addition, the aforementioned blades can have straight cutting edges, outer concave cutting edges or convex cutting edges.

The suture attachment means of the present invention can comprise a tail portion having a channel formed or drilled within it for secure surrounded receipt of an end of the suturing material. In this embodiment, the channel is then swaged about the end of the suture material that is inserted in the needle.

BRIEF DESCRIPTION OF THE DRAWINGS

FIG. 1 of the drawings is a perspective view from the front and side of surgical needle 9 showing the cutting edge means 26 and in particular cutting blades 19, 20 and 21 attached to the tail portion 12 adjacent to the suturing material 17;

FIG. 2 of the drawings is an enlarged partial view of surgical needle 9 of FIG. 1 taken along line 2—2 of FIG. 1 and viewed in the direction of the arrows and, in particular, the tail portion 12 of the invention showing in particular the cutting edges 22 and 23 of blades 19 and 20 mounted on the tail portion 12 of needle 9;

FIG. 3 of the drawings is a side elevational view of another preferred embodiment of the invention showing surgical needle 63 and single cutting blade 65 mounted on the inside concave surface 68 at tail portion 78 thereof;

FIG. 4 of the drawings is an enlarged partial view of surgical needle 63 of FIG. 3 taken along line 4—4 of FIG. 3 and viewed in the direction of the arrows, showing tail portion 78 and single blade 65.

FIG. 5 of the drawings is a side elevational view of another preferred embodiment of the present invention and in particular, needle 89 being held by needleholder 98 having a different tip configuration at first end 81 and two convex cutting edges 85 and 86 mounted on blades 83 and 84 attached at the tail portion 96 of needle 89;

FIG. 6 of the drawings is an enlarged partial view of needle 89 taken along line 6—6 of FIG. 5 and viewed in the direction of the arrows, showing the tail portion 96 of the embodiment of needle 89 shown in FIG. 5;

FIG. 7 is an enlarged partial cross-sectional view with cross hatching omitted taken along line 7—7 of FIG. 1, viewed in the direction of the arrows, of tail portion 12 showing blades 19, 20 and 21 projecting radially from the outer periphery 25 of tail portion 12;

FIG. 8 is a partial cross-sectional view with cross hatching omitted of an alternative cutting blade construction to that shown in FIG. 7, having a single cutting surface 36 leading to cutting edge 37 provided on cutting blade 34;

FIG. 9 is an enlarged cross-sectional view with cross hatching omitted of an alternative to the cutting blade arrangement shown in FIGS. 7 and 8 employing a dual cutting blade 40 and 41 arrangement;

FIG. 10 is an enlarged partial cross-sectional view with cross hatching omitted of an alternative single, radially projecting cutting blade 49 embodiment;

FIG. 11 is an enlarged partial front elevational view of an alternative "spatula" type tip configuration;

FIG. 12 is an enlarged front elevational view of another alternative tip configuration employing a flatter "spatula" type tip;

FIGS. 13, 14 and 15 are schematic views of a finished, knotted suture 101 being rotated by needleholder 98, so as to bury knot 12 below the surface of tissue 100;

FIG. 16 is a top plan view of track or opening 104 formed by a suturing needle of the type shown in FIGS. 3, 4, or 10, having central axial passageway 105 and adjacent radial incision 106 and knotted suture 101 extending therefrom and above the surface tissue 100;

FIG. 17 is a partial cross-sectional view taken along lines 17—17 and in the direction of the arrows of FIG. 16 showing track 104 cut into the tissue by the needle and knotted suture 101 being rotated by needleholder 98 so as to bring knot 102 closer to the surface of tissue 100;

FIG. 18 shows knotted suture 101 continuing to be rotated within track 104 formed by the needle so as to bury knot 102 below the surface of the tissue 100; and FIG. 19 is a schematic view showing suture A being rotated in the direction of the arrow since knot 102 is closer to opening 103, while suture B is rotated in the opposite direction since knot 102 is closer to opening 104.

DETAILED DESCRIPTION OF THE DRAWINGS

While this invention is susceptible of embodiment in many different forms, there is shown in the drawings and will herein be described in detail, several specific embodiments, with the understanding that the present disclosure is to be considered as merely an exemplification of the principles of the invention and is not intended to limit the invention to only the embodiments illustrated.

A number of preferred embodiments of the present invention comprising curved surgical needles 10 intended to be used for ophthalmic or other forms of microsurgery and the like are shown in FIGS. 1-10, 18 and 19, and in particular for wound closure of the delicate tissues encountered in such ophthalmic or plastic surgery. The needles of the present invention can be formed of a sutable stainless steel alloy. A first preferred embodiment of needle 9 is shown in FIGS. 1, 2 and 7. Body portion 10 is comprised of a first end having point portion 11 terminating in pointed tip 27, a second end having tail portion 12 and an intermediate portion 13 between the point portion 11 and the tail portion 12. Body portion 10 is substantially curved and has an outer, rounded convex surface 14 and an inner concave surface 15.

The cross-sectional area of body portion 10 in the first preferred embodiment gradually increases as one moves away from the tip portion 11 and through the intermediate portion 13. However, the cross-sectional area of body portion 10 can also be made to either stay constant, gradually thicken or gradually become thinner between the intermediate portion 13 and the tail portion 12. Moreover, no cutting surfaces or edges are provided on intermediate portion 13 between tip portion 11 and cutting edges means 26 of tail portion 12, so as to provide an intermediate portion 13 that is devoid of cutting surfaces. Inner concave surface 15 can be provided with longitudinal ribs 16 as well as provided with one or more flattened regions, so as to aid in gripping and retaining needle 9 within needleholders, other such surgical instruments, and avoid undesired turning, twisting or translation of needle 9 while it is first being pushed through the tissue and then pulled through the tissue by the needleholder, from the other side of the incision.

As shown in FIG. 1, tail portion 12 or needle body portion 10 can be substantially straight, instead of curved like the remainder of needle 9. Tail portion 12 is provided with cutting edge means 26 comprising, in a first preferred embodiment, three substantially triangularly shaped cutting blades 19, 20 and 21, which project radially outwardly from tail portion 12. Suturing material 17 is securely attached to needle by swaging or the like and projects outwardly from tail portion 12 of needle 9 beyond end edge 18. A channel or hole is provided in end 18 of needle 9. This channel can be provided with internal teeth to grip the end of suture material 17 inserted therein. Alternatively, the channel may be devoid of such teeth, wherein the end of the suturing material 17 is placed into the channel and secured by swaging the sides of the channel about the suture end. Suture material 17 can be of any suitable absorbable material, such as a monofilament polyester fiber, a nylon fiber, or a polypropylene material.

As shown in FIGS. 2 and 7, blades 19 and 21 and, 19 and 20 are arranged in substantially perpendicular relation to one another about the outer periphery 25 of tail portion 12. Though not shown, blades 19, 20 and 21 can be otherwise arranged about the periphery 25 of tail portion 12; for instance, having blades 19, 20 and 21 equally spaced about the periphery 25 of tail portion 12, so as to define angles of 120° therebetween when viewed along a plane of cross-section perpendicular to the axial direction of body portion 10, such as that of FIG. 7. In a first preferred embodiment the intermediate portion 13 of body portion 10 is substantially circular in cross-section.

As shown in FIG. 7, blades 19, 20 and 21 are attached to outer periphery 25 of tail portion 12 at attachment regions 29, 30 and 31, respectively. Blades 19, 20 and 21 can be securely attached to body portion 10 by any one of a number of ways, such as brazing or soldering. Alternatively, blades 19, 20 and 21 can be machined into body portion 10.

As shown in FIGS. 1 and 2, blades 19, 20 and 21 widen as one moves towards end edge 18 of tail portion 12, along lines A-B as shown in FIG. 2. The narrower, first ends of blades 19 and 20 are indicated by points A and the wider, second ends of blades 19 and 20 are indicated by points B. FIG. 7 shows that in a first preferred embodiment, each of triangular blades 19, 20 and 21 are constructed like blade 20 having cutting surfaces 32 and 33 which converge linearly to form sharpened cutting edge 23. Blades 19 and 20 are similarly provided with single cutting edges 22 and 24, respectively. Though not shown, blades 19, 20 and 21 can be made to extend beyond end 18 of body portion 10, as well.

FIGS. 11 and 12 illustrate alternative configurations of tip 27 used for initial piercing of the tissue being sutured, which instead of the substantially round cross-section of tip portion 11 described in FIG. 1, the tip has a more blade-like or "spatula" type construction. Specifically, sharpened cutting surfaces 111 and 112 which meet along line 114, define piercing point 110 and cutting edges 115 and 116. Inside surface 113 is a concave surface. FIG. 12 illustrates an alternative "spatula" type tip construction wherein cutting surfaces 121 and 122 are narrower than those of the version shown in FIG. 11. Surfaces 121 and 122 define cutting edges 125 and 126 and piercing point 120, as well as inside concave surface which is relatively larger than that of FIG. 11.

FIG. 8 illustrates another embodiment of needle 9 wherein one or more blades 34 having the configuration shown therein, are provided in attached relation to outer periphery 25 of tail portion 12, along attachment region 39. Single curved, cutting surface 36 ends in sharpened cutting edge 37.

A dual blade alternative embodiment is shown in FIG. 9 wherein blades 40 and 41 are arranged in a radially linear fashion along the outer periphery 25 of tail portion 12. However, blades 40 and 41 could otherwise be arranged along the outer periphery 25 of tail portion 12. Blades 40 and 41 are attached to outer periphery 25 of tail portion 12 along attachment regions 51 and 52. Blades 40 and 41 are provided with curved cutting surfaces 43 and 44, and 46 and 47 respectively—which, in turn, define sharpened cutting edges 45 and 48 respectively.

Shown in FIG. 10 is an alternative single blade construction wherein blade 49 is attached to outer periphery 25 of tail portion 12 along the attachment region 53 and cutting surfaces 50 and 54 which converge to define cutting edge 55. Any of the blade configurations shown in FIGS. 2, 4 and 6-10 can be used with any of the needle configurations of FIGS. 1, 3, 5, 11 or 12.

Another preferred embodiment of the present invention is shown in FIGS. 3 and 4. Body portion 71 of needle 63 comprises first end portion 61 and second end portion 62. Intermediate portion 69 extends between the tail portion at second end 62 and the point portion of first end 61. A knife edge 74 is provided at first end portion 61 and extends between ends 72 and 73 of knife edge 74. Underside 75 of knife edge 74 can also be sharpened so as to provide a cutting edge. Convex outer surface 69 of body portion 63 is substantially rounded in the transverse direction. Substantially flat sides 64 and 70 converge to form inner concave edge 68 of body portion 63; so as to provide a triangular cross section at intermediate position 69.

As further shown in FIGS. 3 and 4, second end portion 62 has blade 65 attached to the outer periphery 79 of tail portion 78 of body portion 71, on inside concave surface 68. Cutting edge 66 provided on blade 65 has a concave outer shape. Moreover, blade 65 can be made to extend past edge 80 of body portion 71. Suture material 80 is securely attached to body portion 71 and extends beyond end 79.

FIGS. 5 and 6 illustrate yet another preferred embodiment of needle 89, among other things, having a lesser degree of curvature than that of the embodiment of FIG. 4. Body portion 76 of needle 89 is shown held by needleholder 98 proximate the intermediate portion 88. First end 81 is provided with concave sides 92 and 93 as well as the top and bottom edges 90 and 91 which taper and converge to a point at the tip of first end portion 81. Intermediate portion 88 has a substantially round cross-section. Top edge 91 of body portion 89 is a convex surface, while inner edge 87 is a concave surface. As shown in FIGS. 5 and 6, second end 82 of body portion 89 is provided with blade elements 83 and 84 at tail portion 96. Blade elements 83 and 84 are provided with convex cutting edges 85 and 86 and increase in width in the direction of end 95, along line A-B of FIG. 6. Suturing material 94, attached to the interior of needle 89, is shown extending from end 95 of tail portion 96.

The various tail portion configurations of the present invention serve a number of significant purposes. Normally, (using the embodiment of FIG. 1 and an example), the tail portion 12 of the needle and in particular end 18, where the suture material commences, encounters the most resistance in passing through the tissue being sutured. Blades 19, 20 and 21 accordingly serve to make radial incisions which project outwardly from the axial bore created in the tissue by the piercing and passage of needle 9. The blades 19, 20 and 21 provided at the end of tail portion 12 make it easier for the end 18 of tail portion 12 (together with suture material 17) to pass through the tissue.

It is especially important that the end 18 of needle 19 and suture material 17 pass smoothly through the tissue, because of the extremely fine thicknesses of suture material 17 usually used in ophthalmatic surgery. Indeed, if the surgeon has to pull excessively on the needle 9 in order to make it pass through the tissue, such extreme tension will be transferred to the suture material and the suture may rupture the surrounding tissue or the suturing material itself may tear. Moreover, point portion 11 and cutting blades 19, 20 and 21 are positioned at opposite ends of the length of needle 9, so as to allow the tissue to recover momentarily from the piercing performed by point portion 11, before the radial incisions are then cut by blades 19, 20 and 21. Accordingly, intermediate portion 13 of body portion 10 is deliberately devoid of cutting surfaces, so that after point portion 11 pierces the tissue and initially creates the axial bore, intermediate portion 13 of body portion 10 merely passes through the axial bore for an interval unit end A of cutting edges 22, 23 and 24 encounter and slice the tissue as they pass through it, thereby creating corresponding radial incisions therein.

The above-described radial incisions in the tissue formed by cutting edge means 26 also serves to facilitate performance of the surgical technique known as "burying the knot". As shown in FIG. 16, when an incision is sutured together during ophthalmatic surgery, knot 102 formed by tying together both ends of the suturing material 101 that has been pulled through the tissue by the needle, is normally formed. However, if the knot is allowed to remain exposed on the exterior surface of the eye tissue, irritation can result as a result of contact with surrounding tissue. Moreover, since it is exposed and visible to the patient, actual or anticipated discomfort can also arise. Accordingly, it has been found desirable to rotate the knotted suture as shown in FIGS. 13, 14 and 15 so that the knot 102 is "buried" below the surface of the tissue 100, as shown in FIG. 18. However, the degree of resistance to such rotation of the suture encountered when conventional ophthalmatic needles (and their corresponding tracks formed by such needles through the tissue) are used, making many surgeons unwilling or unable to rotate such sutures for fear of tearing the suture or repturing the surrounding tissue.

The present invention therefore provides for facilitated rotation of such sutures. Specifically, once needle 9 has moved through the tissue and the corresponding track opened therethrough for the suture material to smoothly pass, the ends of the suture 101 are tied, resulting in exposed knot 102. Needleholders 98, or other similar instruments are then used to grab and rotate the knotted suture 101 from opening 103 to opening 104, so as to move knot 102 in the direction of the arrows, as shown in FIG. 13. The rotation of the knot 102 and suture 101 by needleholder 98 is continued, as shown in FIG. 14, in the direction of the arrow, as knot 102 approaches opening 104 formed in tissue 100 by a needle such as 9. Specifically, as shown in FIGS. 17 and 18, needleholder 98 is used to rotate the tied loop comprising suture 101 so that knot 102 will pass into track 106 formed by a needle such as 63, and eventually be "buried" below the surface of tissue 100. FIG. 15 shows suture 101, with its knot "buried" within the track 106 formed by a needle such as 9.

The radial incisions cut by blades such as 19, 20 and 21 which actually communicate with the axial passageway formed by the point and body portion of the needle, serve to enable the central axial passageway of the track formed by the needle, to expand to receive the knot which may otherwise be too large to fit into the axial passageway. FIGS. 16, 17 and 18 show a knot 102 of a suture 101 being rotated into a track 106 formed by a needle having a construction such as that shown in FIGS. 4 or 10, and, with reference to FIG. 16, creating an opening 104 in tissue 100 comprising an axial bore 105 and adjoining radial incision 106. Radial incision 106 enables bore 105 to effectively expand to facilitate passage of suture 101 therethrough, as well as to receive knot 102 therein, as shown in FIGS. 17 and 18.

With reference to FIG. 19, a knotted suture 101 may be rotated in either a clockwise or counter-clockwise direction depending upon which direction will result in the lesser amount of rotation of the suture 101 to achieve burying of the knot 102 below the surface of the tissue. For instance, with knot 102 positioned closer to opening 103 as shown by suture A of FIG. 19, suture 101 would most easily be rotated in the direction of the arrow, i.e. in the aforementioned manner towards opening 103. Conversely, with knot 102 positioned closer to opening 104, as shown by suture B of FIG. 19, suture 101 would most easily be rotated in the direction of opening 104.

The present invention further comprises a method for suturing an incision made in human or other animal tissue 100 by using suturing material 17 to draw the incision together, and using a surgical needle 9 having a pointed first end 27 and the suturing material 17 attached at a second end comprising the following steps: piercing the surface of the tissue 100 with the point 27 of the needle 9 on one side of the incision; and pushing the needle 9 through the tissue 100 on one side of incision 103, across the incision below the surface of the tissue and up through the opposite side of the incision 104 and above the surface thereof, so as to create an axial bore 105 for the suture material 17 to pass and at least one radial incision 106 emanating therefrom. The needle 9 is then pulled completely through the tissue from the top of the opposite side 104 of the incision. The ends of the suture material are then tied together so as to bring the incision together and from a knot 102. The suturing material 17 is then detached from the needle 9 and the tied suture material 101 is then rotated so as to bury the knot 102 below the surface of the tissue 100.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A curved surgical needle for tissue wound closure, and in particular, suturing tissue together both sides of an incision made in human or animal tissue, having an inner concave surface and an outer convex surface and having suturing material securely attachable thereto, said needle comprising:

a substantially curved body portion having first and second ends;

a point located at said first end of said body portion, for piercing said tissue on opposite sides of said incision and forming an axial passage in said tissue for said suturing material to pass through and thereby draw both sides of said incision together;

suture attachment means positioned at said second end of said body portion and adapted for receiving, securing and maintaining said suturing material upon said needle;

a tail portion proximate said body portion second end;

an intermediate portion between said point and said tail portion devoid of cutting surfaces; and said tail portion having cutting edge means projecting radially outwardly therefrom for making at least one radial cut in said tissue extending from said axial passageway so as to facilitate the entry and passage of said suturing material through said tissue.

2. The invention according to claim 1 wherein said needle further comprises at least one cutting edge proximate said first end of said body portion.

3. The invention according to claim 1 wherein said intermediate portion of said body portion is substantially circular in cross-section.

4. The invention according to claim 1 wherein said needle gradually increases in cross-sectional area from said first end of said body portion to said intermediate portion.

5. The invention according to claim 1 wherein said needle further comprises a substantially flattened area on the concave surface thereof between said first end and said second end of said body portion.

6. The invention according to claim 1 wherein said tail portion cutting edge means comprises at least one blade operably attached to said tail portion.

7. The invention according to claim 1 wherein said tail portion cutting edge means comprises a single blade projecting outwardly from the outer periphery of said tail portion.

8. The invention according to claim 1 wherein said tail portion cutting edge means comprises two blades projecting outwardly from opposite sides of said tail portion.

9. The invention according to claim 1 wherein said tail portion cutting edge means comprises three blades spaced around and projecting outwardly from the outer periphery of said tail portion.

10. The invention according to claim 6 wherein at least one of said blades has an outer concave cutting edge.

11. The invention according to claim 1 wherein at least one of said blades has an outer convex cutting edge.

12. The invention according to claim 1 wherein said suture attachment means comprises said tail portion having a channel for secure surrounded receipt of an end of said suturing material.

13. The invention according to claim 12 wherein said suture attachment means further comprise said channel being swaged about said end of said suture material.

* * * * *

UNITED STATES PATENT AND TRADEMARK OFFICE
CERTIFICATE OF CORRECTION

PATENT NO. : 4,799,483
DATED : January 24, 1989
INVENTOR(S) : Manus C. Kraff

It is certified that error appears in the above-identified patent and that said Letters Patent is hereby corrected as shown below:

| | |
|---|---|
| Col. 3, Line 44 | After "knot" delete "12" and insert instead --102-- |
| Col. 6, Line 39 | After "1" delete "and" and insert instead --as-- |
| Col. 6, Line 68 | After "interval" delete "unit" and insert instead --until-- |
| Col. 7, Line 8 | After "surgery," delete "knot" and insert instead --a knot-- |
| Col. 7, Line 23 | After "used," delete "making" and insert instead --makes-- |
| Col. 7, Line 25 | After "or" delete "repturing" and insert instead --rupturing-- |
| Col. 8, Line 36 | After "suturing" delete "tissue" |

Signed and Sealed this

Nineteenth Day of December, 1989

*Attest:*

JEFFREY M. SAMUELS

*Attesting Officer*   *Acting Commissioner of Patents and Trademarks*